United States Patent [19]

Yandell

[11] Patent Number: 5,613,251
[45] Date of Patent: Mar. 25, 1997

[54] LOCKING RAPE PREVENTION BELT

[76] Inventor: Clifford N. Yandell, 2056 - 50th Ave., Vero Beach, Fla. 32966

[21] Appl. No.: 616,286

[22] Filed: Mar. 15, 1996

[51] Int. Cl.⁶ .................................................. A41D 3/00
[52] U.S. Cl. ................................ 2/338; 2/311; 2/312
[58] Field of Search ......................... 2/300, 301, 302, 2/303, 304, 305, 306, 307, 308, 309, 310, 311, 312, 313, 314, 315, 316, 317, 318, 319, 320, 321, 322, 323, 324, 325, 326, 328, 329, 330, 331, 332, 333, 334, 335, 336, 337, 338, 339, 340, 341, 342, 400, 403, 406, 218; 24/517

[56] References Cited

U.S. PATENT DOCUMENTS

| | | | |
|---|---|---|---|
| 33,162 | 8/1861 | Reynolds | 128/883 |
| 104,117 | 8/1870 | Cook | 128/883 |
| 1,353,483 | 9/1920 | Leins | 2/339 |
| 2,220,593 | 11/1940 | Watson | 2/339 |
| 2,400,844 | 5/1946 | Segal | 2/339 |
| 4,575,873 | 3/1986 | Smith | 2/218 X |
| 4,599,751 | 7/1986 | Bouwhuis | 128/883 |
| 5,243,710 | 9/1993 | Graycroft | 2/338 X |
| 5,368,050 | 11/1994 | Donelan | 2/406 |
| 5,485,636 | 1/1996 | Yandell | 2/406 |

*Primary Examiner*—Jeanette E. Chapman
*Attorney, Agent, or Firm*—Alvin S. Blum

[57] ABSTRACT

A device to prevent rape of a person wearing trousers or shorts is in the form of a locking, cut resistant belt that has the external appearance of an ordinary belt. A flexible, cut resistant cable is secured to the underside of the belt. A special clasp is attached to one end of the cable. The other end of the cable is engaged by the clasp at adjustable distances from the end to thereby snugly encircle the waist with the belt. The clasp is locked in the cable engaged position by a small padlock held within an elastic pocket. The clasp, padlock and pocket are all concealed flat against the underside of the belt.

7 Claims, 1 Drawing Sheet

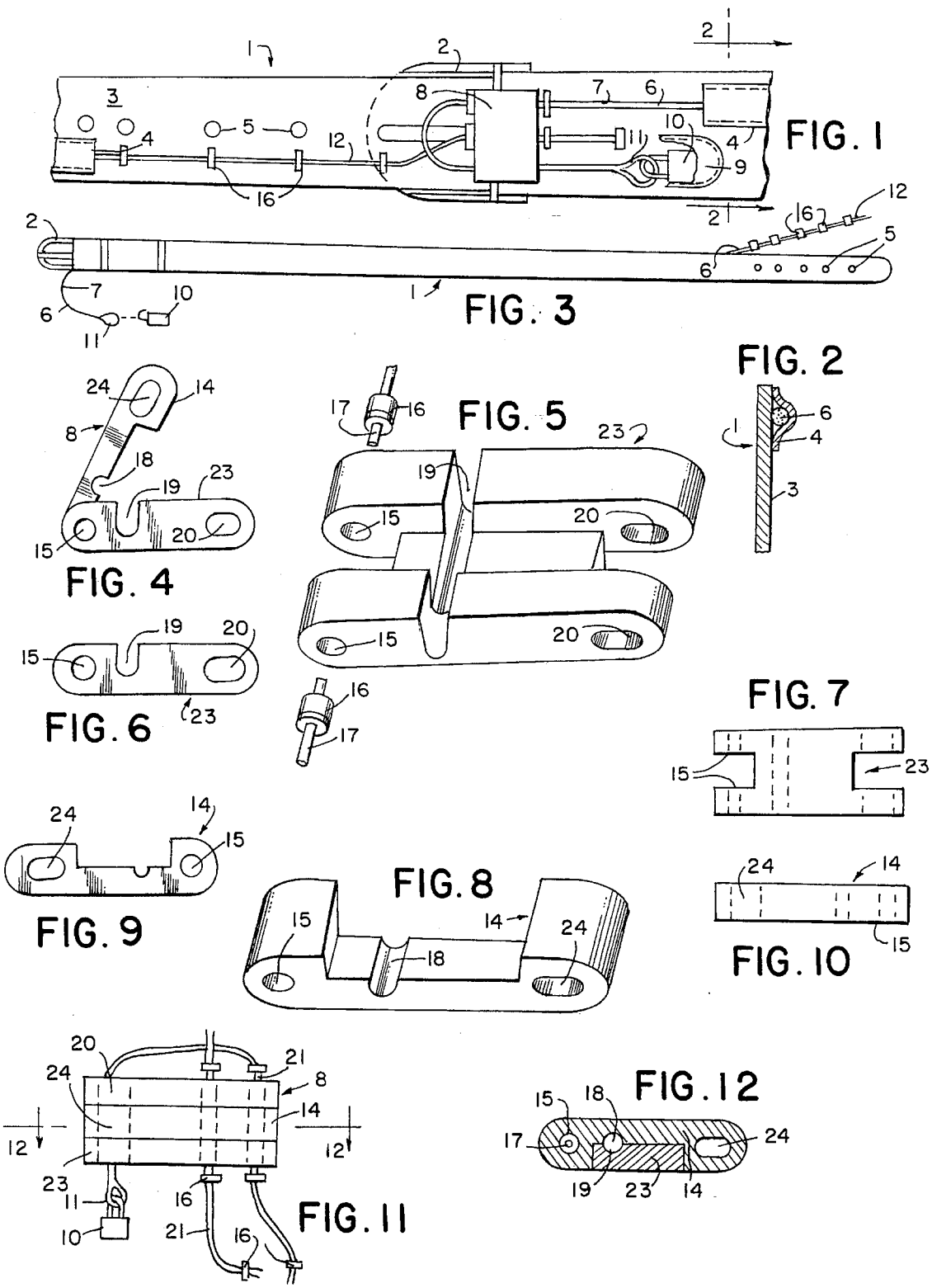

LOCKING RAPE PREVENTION BELT

FIELD OF THE INVENTION

This invention relates to rape prevention devices, and, more particularly, to a lockable belt for women's trousers and shorts that is cut resistant.

BACKGROUND OF THE INVENTION

The applicant, in U.S. Pat. No. 5,485,636 issued Jan. 23, 1996 discloses a protective undergarment formed from cut-resistant cable that forms a web covering the crotch. A unique locking arrangement locks the cable around the legs and waist. The undergarment prevents access by a rapist without the key or combination.

U.S. Pat. No. 4,599,751 issued Jul. 15, 1986 to Bouwhuis discloses a chain mail pants with close fitting legs and a lockable belt for this purpose. This would have to be custom fitted so that access could not be attained by pushing the garment aside at the legs. It would also be quite confining and uncomfortable.

It is well known that rape of females is most often done by a friend or acquaintance. Date rape is most common, especially if one or both parties become inebriated or the male becomes persistent and forceful. If the female decides beforehand that she will not engage in intercourse, it would be very helpful if that determination could somehow be translated into a positive action that would prevent intercourse.

In most of these situations, the potential rapist is not so aggressive as to actually try to cut off the woman's clothing to gain access if he cannot undress the victim. If the woman is wearing shorts or trousers with a belt, the woman will be protected against rape in these situations if the prospective rapist cannot open the belt. A belt that cannot be opened without the wearer's cooperation would be rape protective in these situations and would be more comfortable and acceptable than the undergarments of the art.

SUMMARY OF THE INVENTION

It is accordingly an object of the invention to provide a belt for trousers and shorts that is cut resistant and lockable. It is another object of the invention to provide a locking means and cut resistant means that are concealed from view and comfortable to wear and convenient to use. It is another object of the invention that the belt have an attractive appearance and be available in a variety of models to satisfy fashion requirements.

The invention comprises a cut resistant cable concealed on the inner aspect of the belt and extending free of the belt at both ends. At a first end the cable terminates in a series of sleeves spaced apart the same distance as the belt adjustment holes on the belt. At a second end of the cable, beneath the belt buckle, a locking latch is affixed to the cable. The cable continues beyond the latch and terminates in an eyelet. The looking latch is comprised of two members which pivot on the cable to which they are attached to an open position. In the open position, the first end of the cable, between any pair of sleeves, is inserted into the latch which is then pivotted to a closed position. In the closed position, the cable cannot be removed from the latch so that the belt cannot be opened and the trousers or shorts removed. To prevent the latch from opening, a hole is both members receives the second end of the cable, the hole being just large enough to receive the eyelet. A padlock is then passed through the eyelet and locked. Now the eyelet cannot be passed through the hole, effectively, locking the belt. An elastic pouch or pocket on the underside of the belt comfortably holds and conceals the small padlock.

These and other objects, advantages and features of the invention will become apparent when the detailed description is studied in conjunction with the drawings, in which like elements in the various figures are indicated by like reference characters.

BRIEF DESCRIPTION OF THE DRAWINGS

FIG. 1 is a plan view of the underside of the belt of the invention with buckle fastened.

FIG. 2 is a sectional view taken through line 2—2 of FIG. 1.

FIG. 3 is a plan view of the top of the belt of FIG. 1 unbuckled.

FIG. 4 is a top view of the clasp in the open position.

FIG. 5 is a perspective front elevation view of the outer portion of the clasp.

FIG. 6 is a top view of the outer portion of the clasp.

FIG. 7 is a rear elevation view of the outer portion of the clasp.

FIG. 8 is a perspective front elevation view of the inner portion of the clasp.

FIG. 9 is a top view of the inner portion of the clasp.

FIG. 10 is a rear elevation view of the inner portion of the clasp.

FIG. 11 is a front elevation view of the assembled and locked clasp.

FIG. 12 is a sectional view taken through line 12—12 of FIG. 11.

DETAILED DESCRIPTION OF PREFERRED EMBODIMENT

Referring now first to FIGS. 1–3, the device comprises a belt 1 of conventional outward appearance that may be made of leather or fabric with any of a number of different styles of buckles 2 as may be dictated by fashion. Waist adjustment holes 5 are conventional. A cut-resistant flexible cable, such as a 3/64 inch diameter multistranded stainless steel cable is concealed on the underside 3 of the belt, secured by a nylon strip 4 sewn to the belt so as to make the belt highly cut resistant. As long as the ends of the cable remain tightly joined together about the waist and through the belt loops of the shorts or trousers of the wearer, the wearer will be reasonably well protected from the most common forms of rape by an acquaintance such as "date rape".

The cable 6 has a first end 7 projecting from the nylon strip 4, and terminating in closed eyelet or locking loop 11. Securely attached to first end 7 of the cable before the loop 11 is clasp 8, which can securely and removably engage the second end 12 of the cable at adjustable distances from its termination so that the cable as well as the belt will snugly fit about the waist of the user to prevent slipping the closed belt off.

Enlargements 16 in the form of swaged sleeves are affixed to the cable at intervals spaced apart on end 12 by distances substantially equal to the spacing between holes 5 in the belt so that belt and cable may be adjusted correspondingly. The clasp 8 clamps on the cable between enlargements, and locking loop, when passed through the clasp, prevents the clasp from opening and releasing end 12. A very small combination or key operated padlock 10, when locked through the loop 11, prevents the loop from being pulled through the clasp to permit the clasp to open and release the cable. An elastic pocket 9, shown partly broken away, holds the padlock snugly against the belt.

Referring now to FIGS. 4–12, the cable clamp or clasp 8 is comprised of two separate pieces, an outer portion 23 and an inner portion 14. At one end is a pivot hole 15 which passes through both pieces. A cable 17 passes through this hole and is held in place by swaged sleeves 16 at both ends so that the clasp cannot be removed and the two pieces pivot on the pivot cable 17. There is a half slot 18 in the inner piece and corresponding half slot 19 in the outer piece. A cable may be laid in this half slot from the side of the clasp when open. When the clasp is closed, pivoting about cable 17, the cable is held captive. When the cable with locking loop 11 is then slipped through slots 20 in the outer piece and slot 24 in the inner piece, the clasp is locked and the cable can only be removed by pulling out the locking loop 11. When the locking loop 11 is engaged by the padlock 10, the cable cannot be removed from the clasp because the locking cable cannot be pulled out of the slots 20, 24. By swaging on multiple sleeves 16, the cable is provided with length adjustments by simply inserting in the clasp an appropriate portion 21 of the cable between sleeves 16. The sleeves 16 are too large to pass through the hole formed by the juxtaposed half slots of the clasp.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

What is claimed is:

1. A cut resistant rape-preventing belt that cannot be removed from the waist of a user without consent, the belt comprising:

(A) a belt having a long axis, a buckle at a first termination, buckle engaging holes spaced apart from one another by interhole spacing at a second termination, an outer surface, and an undersurface;

(B) a cut resistant elongate flexible cable securely attached to the undersurface of the belt, the cable having a first end and a second end;

(C) a clasp means for securely engaging the cable at adjustable distances from the second end, the clasp means securely attached to the first end of the cable; and (D) locking means for maintaining the clasp means in securely engaging operation on the cable at adjustable distances from the second end so that the belt may be worn snug fitting about the waist and preventing removal thereof without the cooperation of the wearer.

2. The belt according to claim 1, in which the cable is provided with enlargements at spaced apart distances, the spaced apart distances corresponding substantially to the interhole spaces, and the clasp means is openable to receive therein a cable portion between the enlargements, and the clasp means is closable to retain therein the cable portion, and the locking means maintains the clasp means in closed condition.

3. The belt according to claim 2, in which the first end of the cable terminates in a closed locking loop and the clasp means is comprised of a first element hingedly joined to a second element by passage of the cable through an aperture in each element, each element being further provided with a complementary passage arranged to pass the cable with locking-loop therethrough so as to maintain the two elements in closed relationship when the locking loop is prevented from being pulled through the passages.

4. The belt according to claim 3, further comprising a padlock for engaging the locking loop to thereby prevent the loop from being pulled through the passages.

5. The belt according to claim 4, further comprising a pocket attached to the underside of the belt to hold therein the padlock.

6. A cut resistant rape-preventing belt that cannot be removed from the waist of a user without consent, the belt comprising:

(A) a belt having a long axis, a buckle at a first termination, buckle engaging holes spaced apart from one another by interhole spacing at a second termination, an outer surface, and an undersurface;

(B) a cut resistant elongate flexible cable securely attached to the undersurface of the belt, the cable having a first end and a second end;

(C) a clasp means for securely engaging the cable at adjustable distances from the second end, the clasp means securely attached to the first end of the cable;

(D) looking means for maintaining the clasp means in securely engaging operation on the cable at adjustable distances from the second end so that the belt may be worn snug fitting about the waist and preventing removal thereof without the cooperation of the wearer and in which the cable is provided with enlargements at spaced apart distances, the spaced apart distances corresponding substantially to the interhole spaces, and the clasp means is openable to receive therein a cable portion between the enlargements, and the clasp means is closable to retain therein the cable portion, and the locking means maintains the clasp means in, closed condition.

7. The belt according to claim 6, in which the first end of the cable terminates in a closed locking loop and the clasp means is comprised of a first element hingedly joined to a second element by passage of the cable through an aperture in each element, each element being further provided with a complementary passage arranged to pass the cable with locking loop therethrough so as to maintain the two elements in closed relationship when locking loop is prevented from being pulled through the passages.

\* \* \* \* \*